United States Patent [19]

Fey et al.

[11] Patent Number: 5,190,971

[45] Date of Patent: Mar. 2, 1993

[54] SUBSTITUTED DIBENZ-OXA-THIOCINONES, -12-OXIDES AND -12,12-DIOXIDES, A PROCESS FOR THEIR PREPARATION AND THEIR USE IN MEDICAMENTS

[75] Inventors: Peter Fey; Klaus Frobel; Jan-Bernd Lenfers, all of Wuppertal; Andreas Knorr, Erkrath; Johannes-Peter Stasch, Wuppertal; Erwin Bischoff, Wuppertal; Hans-Georg Dellweg, Wuppertal; Martin Beuck, Haan, all of Fed. Rep. of Germany

[73] Assignee: Bayer Aktiengesellschaft, Leverkusen, Fed. Rep. of Germany

[21] Appl. No.: 798,386

[22] Filed: Nov. 26, 1991

[30] Foreign Application Priority Data

Dec. 13, 1990 [DE] Fed. Rep. of Germany ....... 4039860

[51] Int. Cl.$^5$ ..................... A61K 31/39; C07D 327/00
[52] U.S. Cl. ......................................... 514/431; 549/10
[58] Field of Search ........................... 549/10; 514/431

[56] References Cited

FOREIGN PATENT DOCUMENTS 3919255 12/1990 Fed. Rep. of Germany .

OTHER PUBLICATIONS

W. Lam et al., *J. Am. Chem. Soc.*, "Diaryltetraoxypersulfuranes", 103, pp. 120–127 (1981).

W. Lam et al., *J. Org. Chem.*, "Restricted Internal Rotations in Some Ortho–Substituted Diaryl Sulfides and Salfones," 46, pp. 4458–4462 (1981).

W. Lam et al., *J. Org. Chem.*, "Ketalization of Dihydroxy Sulfones (8–S–4 Species) by Cyclodehydration," 46, pp. 4462–4468 (1981).

Urs T. Ruegg, "Ouabain—The Cause of Hypertension", Neue Zuricher Zeitung, Mar. 4, 1992.

Johannes-Peter Stasch, "Rapid Communication: Dynorphin Stimulates the release of ANP from isolated rat atria", Nov. 25, 1988, pp. 101–102.

James A. Pitcock, M.D., "Renomedullary Deficiency in Partial Nephrectomy-Salt Hypertension," in Hypertension, vol. 2, No. 3, 1980, pp. 281–290.

T. Sassa et al., "Structure of peniccilide, a new metabolite ... ", Tetrahedron Letters, No. 45, (Nov. 1974), pp. 3941–3942.

*Primary Examiner*—Richard L. Raymond
*Assistant Examiner*—Mark W. Russell
*Attorney, Agent, or Firm*—Sprung Horn Kramer & Woods

[57] ABSTRACT

The invention relates to substituted dibenz-oxa-thiocinone-12-oxides and -12,12-dioxides of the general formula I

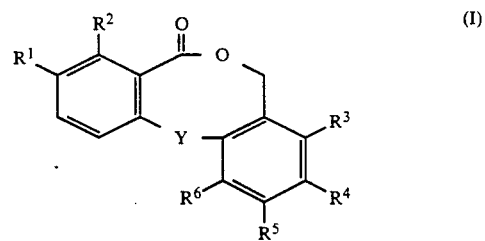

in which $R^1$ to $R^6$ and Y have the meaning indicated in the description, to processes for their preparation and to their use in medicaments, in particular in circulation-influencing medicaments.

5 Claims, No Drawings

SUBSTITUTED DIBENZ-OXA-THIOCINONES, -12-OXIDES AND -12,12-DIOXIDES, A PROCESS FOR THEIR PREPARATION AND THEIR USE IN MEDICAMENTS

The invention relates to substituted dibenz-oxa-thiocinones, -12-oxides and -12,12-dioxides, to a process for their preparation and to their use in medicaments, in particular in circulation-influencing medicaments.

Some diaryltetraoxypersulphuranes are already known from the publications J. Org. Chem. 1981, 46, 4462–4468 and J. Am. Chem. Soc. 1981, 103, 120–127.

The present invention relates to compounds of the general formula (I)

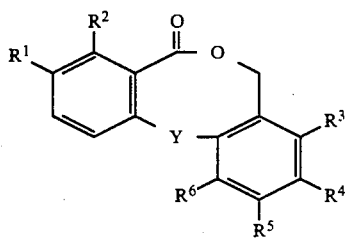

in which
$R^1$ and $R^6$ are identical or different and each represent hydrogen, or represent straight-chain or branched alkyl or alkenyl each having up to 10 carbon atoms which are optionally monosubstituted to trisubstituted by halogen, azido or imino or by cycloalkyl having 3 to 8 carbon atoms or aryl having 6 to 10 carbon atoms, which in turn are optionally monosubstituted or disubstituted by identical or different substituents from the series comprising halogen, nitro, cyano, hydroxyl and straight-chain or branched alkyl, alkoxy or alkoxycarbonyl each having up to 6 carbon atoms, or alkyl or alkenyl which are optionally additionally substituted by a group of the formula $-OR^7$, $-CO-R^8$ or $-CONR^9R^{10}$,
in which
$R^7$ denotes hydrogen, cycloalkyl having 3 to 7 carbon atoms or straight-chain or branched alkyl, alkenyl or acyl each having up to 8 carbon atoms, which are optionally monosubstituted to trisubstituted by halogen-substituted phenyl, cycloalkyl having 3 to 7 carbon atoms, hydroxyl, halogen or straight-chain or branched alkoxy having up to 6 carbon atoms or by carboxyl, acyl having up to 6 C atoms or alkoxycarbonyl having up to 6 C atoms,
$R^8$ denotes hydrogen, hydroxyl, phenoxy or straight-chain or branched alkoxy having up to 8 carbon atoms, or denotes aryl having 6 to 10 carbon atoms, or cycloalkyl having 3 to 8 carbon atoms, which are optionally substituted by hydroxyl or halogen or by straight-chain or branched alkyl, alkoxy or alkoxycarbonyl each having up to 8 carbon atoms, or denotes straight-chain or branched alkyl or alkenyl each having up to 8 carbon atoms, which are optionally substituted by halogen, carboxyl, hydroxyl or alkoxy, alkoxycarbonyl or acyl each having up to 6 C atoms,
$R^9$ and $R^{10}$ are identical or different and denote hydrogen, straight-chain or branched alkyl having up to 8 carbon atoms or phenyl, or $R^1$ and/or $R^6$ directly represent a group of the formula $-OR^7$ or $-CO-R^8$,
in which
$R^7$ and $R^8$ have the abovementioned meaning,
$R^2$ represents hydrogen, or represents the group $-OR^7$,
in which
$R^7$ has the abovementioned meaning, or represents straight-chain or branched alkyl or alkenyl each having up to 8 carbon atoms, which are optionally substituted by the group $-OR^7$,
in which
$R^7$ has the abovementioned meaning, or represents phenyl which is optionally monosubstituted to trisubstituted by halogen, nitro or hydroxyl or by straight-chain or branched alkoxy having up to 6 carbon atoms,
$R^3$, $R^4$ and $R^5$ are identical or different and represent hydrogen, nitro, halogen or straight-chain or branched alkyl having up to 8 carbon atoms,
Y represents a sulphur atom or the group of the formula $>SO$ or $>SO_2$,
and their physiologically acceptable salts, with the proviso that if Y represents the $>SO-$ or $>SO_2$-group, at lest one of the substituents $R^1$-$R^6$ must be different from hydrogen.

Physiologically acceptable salts can be salts of the compounds of general formula (I) according to the invention with inorganic or organic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, benzenesulphonic acid, toluenesulphonic acid or naphthalenedisulphonic acid.

Physiologically acceptable salts can also be salts of the compounds of the general formula (I) (in the case of the carboxylic acids) with bases. Appropriate cations are then, for example, physiologically tolerable metal cations or ammonium cations. Of these, preferred cations are alkali metal cations or alkaline earth metal cations such as, for example, sodium cations, potassium cations, magnesium cations or calcium cations, and also aluminium cations or ammonium cations, and also non-toxic substituted ammonium cations of amines such as di-lower alkylamines, tri-lower alkylamines, dibenzylamine, N,N'-dibenzylethylenediamine, N-benzyl-β-phenylethylamine, N-methylmorpholine or N-ethylmorpholine, dihydroabietylamine, N,N'-bis(dihydroabietyl)ethylenediamine, N-lower alkylpiperidine and other amines which can be used for the formation of salts.

The compounds of the general formula (I) according to the invention may exist in stereoisomeric forms which behave as image and mirror image (enantiomers) or which do not behave as image and mirror image (diastereomers). The invention relates both to the antipodes and to the racemic forms and also the diastereomer mixtures. The racemic forms can be separated, like the diastereomers, into the stereoisomerically uniform constituents in a known manner [cf. E. L. Eliel, Stereochemistry of Carbon Compounds McGraw Hill, 1962[.

Preferred compounds of the general formula (I) are those in which
$R^1$ and $R^6$ are identical or different and represent hydrogen or straight-chain or branched alkyl or alkenyl each having up to 8 carbon atoms which are optionally monosubstituted or disubstituted by fluorine, chlorine, bromine or iodine or by cyclopropyl, cyclopentyl, cyclohexyl or phenyl, which in turn are optionally substituted by fluorine, chlorine or hydroxyl or by straight-chain or branched alkyl or alkoxy each having up to 4 carbon atoms, or alkyl or alkenyl which are optionally additionally substituted by a group of the formula $-OR^7$, $-CO-R^8$ or $-CONR^9R^{10}$, in which $R^7$ denotes hydrogen, cyclopentyl, cyclohexyl or straight-chain or branched alkyl or acyl each having up to 6 carbon atoms, which are optionally substituted by chlorine-substituted phenyl, cyclopropyl, cyclopentyl, cyclohexyl, hydroxyl, fluorine, chlorine, bromine or straight-chain or branched alkoxy having up to 4 carbon atoms or by carboxyl, acyl or alkoxycarbonyl having up to 6 C atoms, $R^8$ denotes hydrogen, hydroxyl, phenoxy or straight-chain or branched alkoxy having up to 6 carbon atoms, or denotes phenyl, cyclopropyl, cyclopentyl or cyclohexyl, which are optionally substituted by hydroxyl, fluorine, chlorine or bromine or by straight-chain or branched alkyl or alkoxy each having up to 6 carbon atoms, or denotes straight-chain or branched alkyl having up to 6 carbon atoms, which is optionally substituted by fluorine, chlorine, bromine, hydroxyl or carboxyl or by alkoxy, acyl or alkoxycarbonyl having up to 6 C atoms, $R^9$ and $R^{10}$ are identical or different and denote hydrogen, straight-chain or branched alkyl having up to 6 carbon atoms, or $R^1$ and/or $R^6$ directly represent a group of the formula $-OR^7$ or $-CO-R^8$, in which $R^7$ and $R^8$ have the abovementioned meaning, $R^2$ represents hydrogen or the group $-OR^7$, in which $R^7$ has the abovementioned meaning, or represents straight-chain or branched alkyl having up to 6 carbon atoms, which is optionally substituted by the group $-OR^7$, in which $R^7$ has the abovementioned meaning, or represents phenyl which is optionally substituted by fluorine, chlorine, bromine, iodine, hydroxyl or straight-chain or branched alkoxy having up to 4 carbon atoms, $R^3$, $R^4$ and $R^5$ are identical or different and represent hydrogen, nitro, fluorine, chlorine, bromine iodine or straight-chain or branched alkyl having up to 6 carbon atoms, Y represents a sulphur atom or a group of the formula $>SO$ or $>SO_2$, and their physiologically acceptable salts, with the proviso that if Y represents $>SO-$ or $>SO_2$-group, at least one of the substituents $R^1$-$R^6$ must be different from hydrogen.

Particularly preferred compounds of the general formula (I) are those in which $R^1$ and $R^6$ are identical or different and represent hydrogen, or straight-chain or branched alkyl or alkenyl having up to 8 carbon atoms, which is optionally monosubstituted or disubstituted by fluorine, chlorine, bromine, iodine or phenyl, which in turn can be substituted by chlorine, hydroxyl, methyl or methoxy, or alkenyl or alkyl which are optionally additionally substituted by a group of the formula $-OR^7$, $-CO-R^8$ or $-CONR^9R^{10}$, in which $R^7$ denotes hydrogen, cyclopentyl or straight-chain or branched alkyl or acyl having up to 4 carbon atoms which are optionally substituted by chlorine-substituted phenyl, hydroxyl, chlorine or methoxy or by carboxyl, acyl or alkoxycarbonyl each having up to 4 C atoms, $R^8$ denotes hydrogen, hydroxyl or straight-chain or branched alkoxy having up to 4 carbon atoms, or denotes phenyl, cyclopropyl, cyclopentyl or cyclohexyl, which are optionally substituted by hydroxyl, fluorine, chlorine or bromine or by straight-chain or branched alkyl or alkoxy each having up to 4 carbon atoms, or denotes straight-chain or branched alkyl having up to 4 carbon atoms, which is optionally substituted by fluorine, chlorine or bromine or by hydroxyl, carboxyl, alkoxy, acyl or alkoxycarbonyl each having up to 4 C atoms, $R^9$ and $R^{10}$ are identical or different and denote hydrogen or straight-chain or branched alkyl having up to 4 carbon atoms, or $R^1$ and/or $R^6$ directly represent a group of the formula $-OR^7$ or $-CO-R^8$, in which $R^7$ and $R^8$ have the abovementioned meaning, $R^2$ represents hydrogen or the group $-OR^7$, in which $R^7$ has the abovementioned meaning, or represents straight-chain or branched alkyl having up to 4 carbon atoms, which is optionally substituted by the group of the formula $-OR^7$, in which $R^7$ has the abovementioned meaning, or represents phenyl which is optionally substituted by fluorine, chlorine, bromine, iodine, hydroxyl or methoxy, $R^3$, $R^4$ and $R^5$ are identical or different and represent hydrogen, nitro, fluorine, chlorine, bromine or iodine, or represent straight-chain or branched alkyl having up to 4 carbon atoms, Y represents a sulphur atom or a group of the formula $>SO$ or $>SO_2$ and their physiologically acceptable salts, with the proviso that if Y represents the $>SO-$ or $>SO_2$-group, at least one of the substituents $R^1$-$R^6$ must be different from hydrogen.

Furthermore, a process for the preparation of the compounds of the general formula (I) according to the invention has been found, characterized in that compounds of the general formula (II)

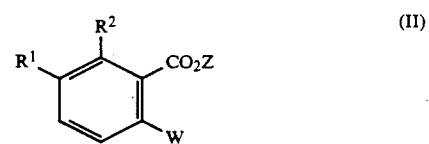

in which $R^1$ and $R^2$ have the abovementioned meaning,

W represents fluorine, chlorine, bromine or iodine, preferably bromine, and

Z represents hydrogen, $(C_1-C_6)$-alkyl, phenyl or a potassium cation or sodium cation, are first condensed in inert solvents with compounds of the general formula (III)

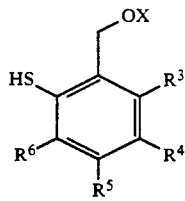   (III)

in which

R³, R⁴, R⁵ and R⁶ have the abovementioned meaning, and

X represents a typical hydroxyl protective group, for example tetrahydropyranyl, with elimination of hydrohalic acids, preferably of hydrobromic acid, to give compounds of the general formula (IV)

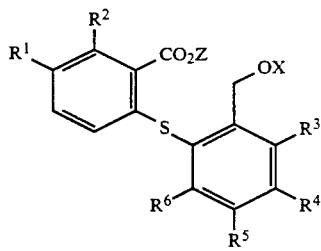   (IV)

in which

R¹, R², R³, R⁴, R⁵, R⁶, X and Z have the abovementioned meaning, then the hydroxyl group is deblocked by a customary method and the compounds are cyclised with elimination of water, it optionally being possible for both the condensation and the cyclisation to be carried out in the presence of a base, an auxiliary and/or a catalyst and the substituents R¹-R⁶ either being introduced into the compounds of the general formula (II) and (III) before condensation or into the compounds of the general formula (IV) after cyclisation by customary methods, such as, for example, substitution, addition or elimination and, if desired, subsequently converted into other functional groups, and in the case in which Y represents the >SO— or >SO₂-group, the dibenz-oxa-thiocinones (Y=S) being oxidised by a customary method, for example with peracids, such as m-chloroperbenzoic acid, or with other customary oxidising agents such as, for example, hydrogen peroxide or sodium metaperiodate.

The process according to the invention is illustrated by way of example by the following equation:

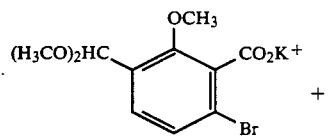

+

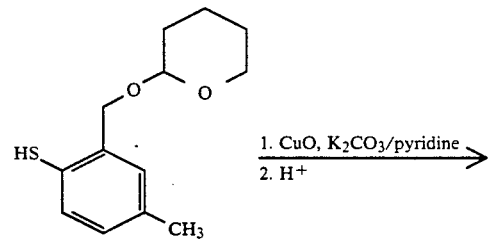

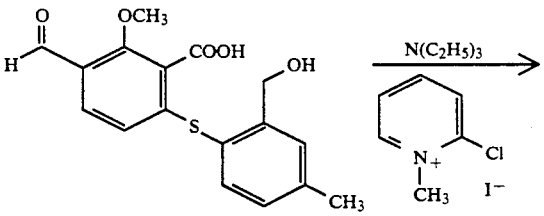

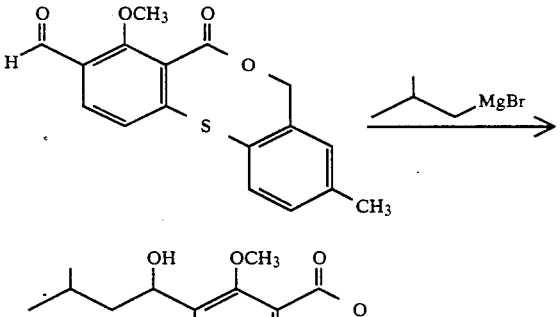

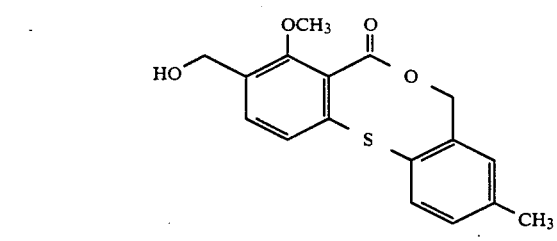

+

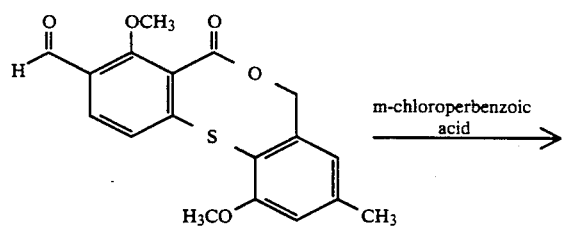

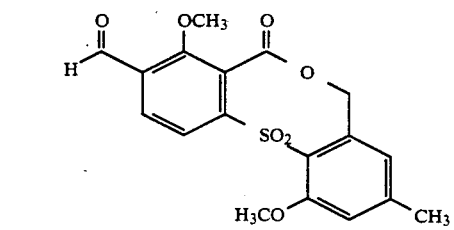

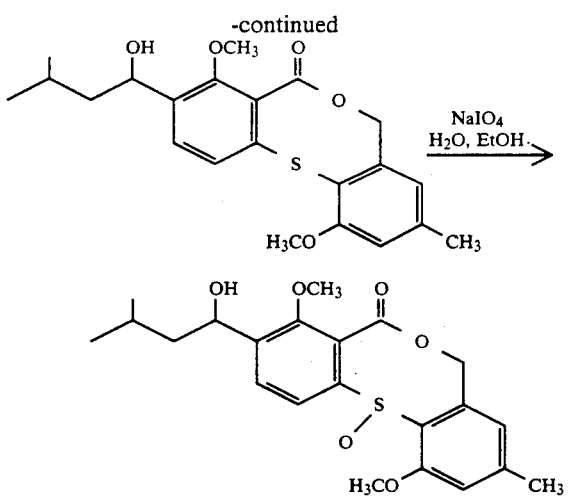

Depending on the particular reaction, water or the customary organic solvents which do not change under the reaction conditions can be used as solvents for condensation, cyclisation and oxidation. These preferably include water, alcohols such as methanol, ethanol, propanol or isopropanol, or ethers such as diethyl ether, dioxane, tetrahydrofuran, glycol dimethyl ether or butyl methyl ether, or ketones such as acetone or butanone, or amides such as dimethylformamide or hexamethylphosphoric triamide, or carboxylic acids such as acetic acid or propionic acid, or dimethyl sulphoxide, acetonitrile, ethyl acetate, or halogenohydrocarbons such as methylene chloride, chloroform or carbon tetrachloride, or pyridine, toluene, xylene, picoline or N-methylpiperidine. Mixtures of the solvents mentioned can also be used. Pyridine and xylene are preferred for condensation and acetonitrile for cyclisation.

Condensation and cyclisation are carried out in a temperature range from +50° C. to +200° C., condensation preferably from +80° C. to +140° C. and cyclisation preferably from +60° C. to +100° C.

The reactions can be carried out at normal pressure, but also at elevated or reduced pressure. In general, they are carried out at normal pressure.

When carrying out the condensation and the cyclisation, any desired ratio of the substances participating in the reaction may be used. In general, however, molar amounts of the reactants are used. The substances according to the invention are preferably isolated and purified by distilling off the solvent in vacuo and recrystallising the residue, which may be obtained in crystalline form only after ice-cooling, from a suitable solvent. In some cases it may be necessary to purify the compounds according to the invention by chromatography.

Suitable bases are the customary inorganic or organic bases. These preferably include alkali metal hydroxides such as, for example, sodium hydroxide, lithium hydroxide or potassium hydroxide, or alkali metal carbonates such as sodium carbonate or potassium carbonate, or alkali metal alkoxides such as, for example, sodium methoxide or potassium methoxide, or sodium ethoxide or potassium ethoxide, or organic amines such as triethylamine, picoline or N-methylpiperidine, or 2-chloro-N-methylpyridinium iodide, or amides such as sodium amide, lithium amide, lithium isopropylamide, or organometallic compounds such as butyllithium or phenyllithium. Potassium carbonate is preferably employed for the condensation, while the cyclisation is preferably carried out using triethylamine and 2-chloro-N-methylpyridinium iodide.

Catalysts employed for the condensation and the cyclisation are, for example, copper salts or oxides, preferably copper oxide and copper(II) acetate, or palladium catalysts such as, for example, [(C$_6$H$_5$)$_3$P]$_4$Pd, or alkali metal iodides such as potassium iodide or sodium iodide, which are added to the reaction mixture in an amount of between 0.5 and 150 mol percent, preferably of 5 to 50 mol percent.

Auxiliaries employed are preferably condensing agents, in particular if a hydroxyl protective group or a carboxyl group activated as the anhydride is present. The customary condensing agents are preferred here, such as carbodiimides, for example N,N'-diethyl-, N,N'-dipropyl-, N,N'-diisopropyl- or N,N'-dicyclohexylcarbodiimide, N-(3-dimethylaminoisopropyl)-N'-ethylcarbodiimide hydrochloride or 2-chloro-N-methylpyridinium iodide.

The oxidation is carried out in the temperature range from 0° C. to +150° C., preferably from 20° C. to +100° C.

The oxidation can be carried out at normal pressure, or at elevated or reduced pressure, preferably at normal pressure.

The introduction and elimination of the hydroxyl protective group is carried out by known methods [Th. Greene, "Protective Groups in Organic Synthesis", 1st edition, J. Wiley & Sons, New York, 1981]. The protective group can be eliminated, for example, by acidic or basic hydrolysis or by hydrogenolysis.

The compounds of the general formulae (II) and (III) are known per se or can be prepared by methods known from the literature [cf. Chem. Ber. 2555 (1928); J. Chem. Soc. Perkin Trans. I, 2973 (1983); Tietze and Eicher, Reaktionen und Synthesen im organisch chemischen Praktikum (Reactions and Syntheses in Practical Organic Chemistry), Georg Thieme Verlag, Stuttgart, New York, 1981; W. Fuerer, H. W. Gschwend, J. Org. Chem. 44, 1133–1136 (1976); F. W. Vierhapper, E. Trengler, K. Kratzl, Monatshefte für Chemie, 106, 1191–1201 (1975); John A. Elix and Vilas Jayanthi, Aust. J. Chem. (1987), 40, 1841–1850].

The compounds of the general formula (IV) are known in some cases or are novel [cf. Collect. Czech. Chem. Commun., 39 (1), 333–54, (1974)] and can then be prepared by the process given above.

The general methods for substituent variation given above preferably include a) alkylation, i.e. reaction with compounds of the general formula (V)

$$R-D \qquad (V)$$

in which

R corresponds to the scope of meaning of one of the substituents $R^1$–$R^6$ given above, but does not represent hydrogen, and D denotes a leaving group such as, for example, chlorine, bromine, iodine or —SO$_2$—(C$_6$H$_5$)—p—CH$_3$, b) a typical Grignard reaction by reaction of a formyl or acyl function with compounds of the general formula (VI)

$$R'-MgBr \qquad (VI)$$

in which R' represents a chemically appropriate completing radical from the scope of meaning of the substituents R¹-R⁶ given above, and c) halogenation with compounds of the general formula (VII)

E—Hal    (VII)

in which E represents one of the substituents R¹-R⁶ given above having the meaning fluorine, chlorine, bromine or iodine or represents the radical —CH₂—NO₂, d) oxidation, for example of an R—CH₂—OH group, in which R has the abovementioned meaning, with reagents such as pyridinium chlorochromate (PCC) or pyridinium dichromate (PDC) to give the corresponding oxo or carboxyl groups, these reactions being carried out in one of the solvents given above, if appropriate in the presence of the auxiliaries and/or catalysts already given, and it being possible to add, if desired, subsequent reactions such as elimination, reduction, oxidation or hydrolysis by methods known from the literature.

The compounds of the formulae (V), (VI) and (VII) are known "cf. J. March "Advanced Organic Chemistry", second edition].

The new compounds of the general formula (I) have an unforeseeable, useful spectrum of pharmacological activity. They influence ANP release, the contractility of the heart, the tone of the smooth musculature and the electrolyte and liquid balance and act both partially or completely as digitalis antagonists or digitalis agonists.

They can therefore be employed in medicaments for the treatment of pathologically modified blood pressure, cardiac insufficiency, and as coronary therapeutics or as a therapeutic in digitalis poisoning.

They can moreover be employed for the treatment of cardiac arrhythmias, renal insufficiency, cirrhosis of the liver, ascites, lung oedema, cerebral oedema, oedema of pregnancy or glaucoma.

The antihypertensive activity of 3-(1-hydroxy-3-methylbutyl)-4,11-dimethoxy-9-methyl-7H-dibenzo[c,f][1,5]oxathiocin-5-one was investigated in rats with "reduced renal mass" hypertension. The "reduced renal mass" (RRM) hypertension was produced by 5/6 nephrectomy with administration of a 0.5% strength saline solution instead of drinking water, following the method described in the literature.

In this form of hypertension, the compounds according to the invention given orally reduce the systolic blood pressure on indirect measurement in conscious rats.

The compounds according to the invention stimulate ANP release in the isolated rat auricle. The ANP concentration in the bath fluid was determined radioimmunologically [J. P. Stasch, H. Grote, S. Kazda, C. Hirth, Dynorphin stimulates the release of ANP from isolated rat atria, Eur. J. Pharmacol. 159, 101 (1989)].

The present invention includes pharmaceutical preparations which contain the compounds according to the invention in addition to non-toxic, inert pharmaceutically suitable excipients, and processes for the production of these preparations.

The abovementioned pharmaceutical preparations may also contain further pharmaceutical active substances in addition to the compounds according to the invention.

The abovementioned pharmaceutical preparations are produced in a customary manner by known methods, for example by mixing the active substance(s) with the excipient(s).

In general, it has proved advantageous to administer the active substance(s) in total amounts of about 0.5 to about 500, preferably 1 to 100 mg/kg of body weight every 24 hours, if appropriate in the form of several individual doses, to achieve the desired results. An individual dose contains the active substance(s) preferably in amounts of about 1 to about 80, in particular 1 to 30 mg/kg of body weight. However, it may be necessary to deviate from the dosages mentioned, in particular depending on the species and body weight of the subject to be treated, the nature and the severity of the disease, the type of preparation and the administration of the medicament and the period of interval within which administration takes place.

Starting Compounds

EXAMPLE 1

3-Methoxy-4-methyl-N-pivaloylaniline

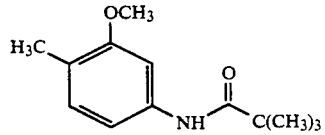

5.1 g (37 mmol) of 3-methoxy-4-methylaniline are dissolved in 70 ml of methylene chloride, and treated with 70 ml of satd. NaHCO₃ solution and with 4.6 ml (37 mmol) of pivaloyl chloride. After stirring vigorously for 12 hours, the organic phase is separated off, washed with 1N hydrochloric acid and water, dried over magnesium sulphate and concentrated in vacuo. The product is obtained in crystalline form and is further processed without further purification.

Yield: 6.2 g (76% of theory) of colourless solid $C_{13}H_{19}NO_2$(221)

¹H-NMR (250 MHz, CDCl₃): δ=1.31, (s, 9H, C(CH₃)₃); 2.18 (s, 3H, Ar-CH₃); 3.83 (s, 3H, OCH₃); 6.71 (dd, 1H, Ar-H); 7.03 (d, 1H, Ar-H); 7.29 (s, 1H, N-H); 7.48 (d, 1H, Ar-H).

MS (EI): 221 (M+), 137

EXAMPLE 2

2-Methoxy-3-methyl-6-N-pivaloylaminobenzoic acid

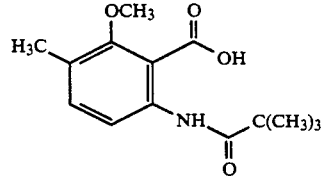

500 ml (0.8 mol) of a 1.6M n-butyllithium soln. in hexane are added dropwise at 0° C. under argon to a solution of 59 g (0.266 mol) of the compound from Example 1 dissolved in 800 ml of abs. tetrahydrofuran and the mixture is stirred at room temperature for 20 hours. In a second flask, 800 ml of tetrahydrofuran are cooled to −70° C. also under argon and treated with 140 g of powdered dry ice. The solution containing the lithiated compound is then slowly added dropwise to the CO₂-containing solution at −70° C. After 10 minutes at −70° C., the solution is slowly warmed to 0° C., diluted with ether, hydrolysed using ice and extracted several times with 1N sodium hydroxide solution. The basic solution is acidified with 2N hydrochloric acid and extracted with ether. The organic phase is dried over magnesium sulphate and concentrated.

Yield: 65.7 g (93% of theory), orange oil
C₁₄H₉NO₄ (265)
¹N-NMR (250 MHz, CDCl₃): δ=1.33 (s, 9H, t-butyl); 2.32 (s, 3H, Ar-CH₃); 3.93 (s, 3H, OCH₃); 7.40 (d, 1H, Ar-H); 8.62 (d, 1H, Ar-H); 11.70 (s, 1H, —COOH).
MW (EI): 265 (M+); 220, 190, 163

EXAMPLE 3

Methyl 6-amino-2-methoxy-3-methylbenzoate

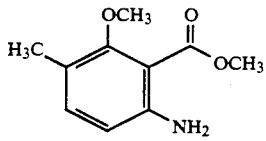

20 g (75 mmol) of the compound from Example 2 are dissolved in 80 ml of methanol, treated with 12 ml of conc. sulphuric acid and 9 ml (82 mmol) of methyl orthoformate and the mixture is heated under reflux for 72 hours. For work-up, the mixture is concentrated in vacuo, taken up in methylene chloride and extracted three times with dilute hydrochloric acid. The aqueous phase is rendered alkaline with conc. sodium hydroxide solution and exhaustively extracted with methylene chloride. The organic phase is then dried over magnesium sulphate and concentrated in vacuo. The title compound is further reacted without further purification.

Yield: 13.1 g (89% of theory) of brown oil
C₁₀H₁₃NO₃ (195)
¹H-NMR (250 MHz, CDCl₃): δ=2.16 (s, 3H, Ar-CH₃); 3.74 (s, 3H, COOCH₃); 3.92 (s, 3H, OCH₃); 4.93 (s, 2H, NH₂); 6.40 (d, 1H, Ar-H); 7.04 (d, 1H, Ar-H).
MS (EI): 195 (M+), 163

EXAMPLE 4

Methyl 6-bromo-2-methoxy-3-methylbenzoate

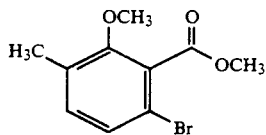

Preparation of the diazonium salt solution: 67.7 g (0.35 mol) of the compound from Example 3 are dissolved in 185 ml of 48% strength hydrobromic acid and 740 ml of water. While stirring and cooling (ice-salt mixture), a solution of 26 g (0.38 mol) of sodium nitrite in 150 ml of water is added dropwise to this solution in such a way that the temperature does not rise above 5° C.

Preparation of the copper(I) bromide solution: 124 g (0.5 mol) of CuSO₄×5 H₂O and 78 g (0.76 mol) of sodium bromide are dissolved with gentle warming in 400 ml of water. A solution of 65 g (0.26 mol) of Na₂SO₃×7 H₂O in 120 ml of water is slowly added dropwise to this solution with stirring. After cooling, the supernatant is decanted off from the colourless precipitate of copper bromide. The precipitate is then dissolved in 190 ml of 48% strength hydrobromic acid.

The diazonium salt solution is added dropwise to the copper(I) bromide solution cooled to 0° C. while stirring vigorously and the mixture is then heated at 80° C. for 12 hours. It is then extracted with methylene chloride, and the organic phase is washed with NaHCO₃ solution, dried over magnesium sulphate, concentrated in vacuo and purified by column chromatography on silica gel using petroleum ether/ethyl acetate 100:1 as eluent.

Yield: 75.6 g (84% of theory), colourless oil
C₁₀H₁₁BrO₃ (259)
¹H-NMR (200 MHz, CDCl₃): δ=2.25 (s, 3H, Ar-CH₃); 3.79 (s, 3H, —COOCH₃); 3.95 (s, 3H, OCH₃); 7.08 (d, 1H, Ar-H); 7.24 (d, 1H, Ar-H).
MS (EI): 260 (M+), 258, 227, 229

EXAMPLE 5

Methyl 6-bromo-3-formyl-2-methoxy-benzoate

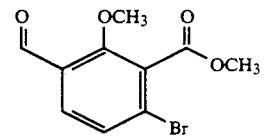

20 ml (0.4 mol) of bromine dissolved in 360 ml of carbon tetrachloride are added dropwise at 80° C. over a period of 5 hours while irradiating with a mercury lamp to 51.5 g (0.2 mol) of the compound from Example 4 dissolved in 1 l of carbon tetrachloride. After a further 90 minutes at 80° C., the mixture is cooled to room temperature and washed with sodium sulphite solution, water and sodium chloride solution. The organic phase is dried over magnesium sulphate and concentrated in vacuo. The benzal bromide thus obtained is treated with 100 ml of conc. sulphuric acid and stirred at room temperature for 30 minutes. For work-up, the mixture is poured onto ice and extracted with ether. The ether phase is washed with water and NaHCO₃ solution, dried over magnesium sulphate and concentrated in vacuo. Purification is carried out by recrystallisation from cyclohexane.

Yield: 44.8 g (82% of theory) of colourless solid
C₁₀H₉BrO₄ (273)
¹H-NMR (200 MHz, CDCl₃): δ=4.00 (s, 3H, OCH₃); 4.01 (s, 3H, OCH₃); 7.49 (d, 1H, Ar-H); 7.78 (d, 1H, Ar-H); 10.30 (s, 1H, CHO).
MS (EI); 274 (M+), 272, 243, 241, 227, 213

EXAMPLE 6

2-Hydroxymethyl-4-methylaniline

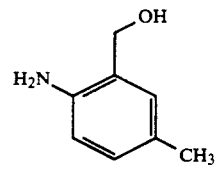

1.3 l of a 1.3 molar lithium aluminium hydride solution in THF are added dropwise under reflux to a solution of 100 g (0.66 mol) of 2-amino-5-methylbenzoic acid in 400 ml of anhydrous tetrahydrofuran. After addition is complete, the mixture is additionally heated under reflux for 1.5 h and hydrolysed at this temperature using a solution of 36 g of potassium hydroxide in 145 ml of water. After boiling under reflux for a further 15 min, the hydroxide precipitate is filtered off while hot, the precipitate is washed with ethyl acetate, the organic solution is concentrated in vacuo, the residue is dissolved in ethyl acetate and the solution is washed with dilute sodium hydroxide solution and water. After drying with sodium sulphate and concentrating the solution, the residue is recrystallised from ethyl acetate.

Yield: 53.3 g (58% of theory) of colourless solid $^1$H-NMR (DMSO): δ=2.15 (s, 3H); 4.3 (d, 2H); 4.6 (s, 2H); 4.9 (tr, 1H); 6.5 (d, 1H); 6.75 (dd, 1H); 6.85 (d, 1H); 6.85 (d, 1H).

EXAMPLE 7

2-Ethoxythiocarbonylthio-5-methyl-benzyl alcohol 19.0 g (0.14 mol) of the compound from Example 6 are dissolved in a mixture of 50 ml of ice and 50 ml of 32% strength hydrochloric acid. While stirring and cooling (ice-salt mixture), a solution of 9.6 g (0.14 mol) of sodium nitrite in 50 ml of water is added dropwise to this solution in such a way that the temperature does not rise above 5° C. The diazonium salt solution thus obtained is added dropwise to a solution of 33.6 (0.2 mol) of potassium methyl xanthate in 50 ml of water warmed to 40°–50° C. After warming at 50° C. for 30 min, the mixture is allowed to cool and is washed three times with ether, the combined ether phases are washed with dilute sodium hydroxide solution and water, the ether phase is dried over sodium sulphate and 18.1 g of crude product are obtained after concentration in vacuo.

Crude yield: 18.1 g (53% of theory) of oil $^1$H-NMR (CDCl$_3$): δ=1.4 (tr, 3H), 2.45 (2s, 3H); 4.65 (m, 4H); 6.95–7.5 (m, 3H).

EXAMPLE 8

4-Ethoxythiocarbonylthio-3-(2-tetrahydropyranyloxymethyl)-toluene 38.2 g (0.158 mol) of the compound from Example 7, dissolved in 500 ml of abs. methylene chloride, are treated with 19.8 g (0.24 mol) of dihydropyran and a spatula tipful of p-toluenesulphonic acid and the mixture is stirred at 25° C. for 14 h. It is washed with aqueous sodium hydrogen carbonate solution and water, dried over sodium sulphate and concentrated in vacuo, and the residue is chromatographed on a silica gel column using petroleum ether.

Yield: 13.7 g (26.6% of theory) of oil.

$^1$H-NMR (CDCl$_3$): δ=1.3 (tr, 3H); 1.4–2.0 (m, 6H); 2.4 (s, 3H); 3.55 (m, 1H); 3.95 (m, 1H); 4.5–5.0 (m, 5H); 7.0–7.6 (m, 3H) ppm.

EXAMPLE 9

4-Methyl-2-(2-tetrahydropyranyloxymethyl)-thiophenol 13.7 g (42 mmol) of the compound from Example 8 are heated overnight under reflux with 9.5 g (0.17 mol) of potassium hydroxide in 70 ml of ethanol. The mixture is concentrated in vacuo, the residue is dissolved in water, the solution is washed with ether, and the aqueous phase is acidified with acetic acid and washed with ether. This ether phase is washed with water, dried over sodium sulphate and concentrated in vacuo.

Crude yield: 7.0 g (70% of theory) of oil $^1$H-NMR (CDCl$_3$): δ=1.5–1.95 (m, 6H); 2.3 (s, 3H); 3.55 (m, 1H); 3.65 (s, 1H); 3.95 (m, 1H); 4.5 (d, 1H); 4.75 (tr, 1H); 4.8 (d, 1H); 7.0 (d, 1H); 7.15–7.3 (m, 2H) ppm.

EXAMPLE 10

Methyl 2-bromo-2-dimethoxymethyl-6-methoxybenzoate 50 g (0.18 mol) of the compound from Example 5, 20 ml (0.18 mol) of trimethyl formate and a spatula tipful of p-toluenesulphonic acid are heated under reflux overnight in 100 ml of methanol. The mixture is concentrated in vacuo, the residue is taken up with ethyl acetate, and the solution is washed with aqueous sodium hydrogen carbonate solution and water, dried over sodium sulphate and concentrated in vacuo.

Yield: 50.7 g (88% of theory) of solid.

$^1$H-NMR (CDCl$_3$): δ=3.35 (s, 6H), 3.85 (s, 3H); 3.95 (s, 3H), 5.55 (s, 1H); 7.35 (d, 1H); 7.45 (d, 1H)) ppm.

EXAMPLE 11

Potassium 2-bromo-5-dimethoxymethyl-6-methoxybenzoate 50.7 g (0.16 mol) of the compound from Example 10 are heated under reflux overnight with 13.4 g (0.24 mol) of potassium hydroxide in 200 ml of methanol and 200 ml of water. The mixture is concentrated in vacuo and the residue is dissolved in water. The solution is washed with ether and freeze-dried.

Yield: 50.1 g (91% of theory) of solid.

EXAMPLE 12

5-Formyl-6-methoxy-2-[2-hydroxymethyl-4-methyl]-phenylthiobenzoic acid

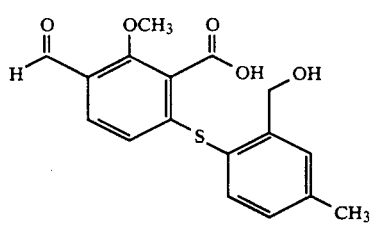

7.0 g (29 mmol) of the compound from Example 9, 3.2 g (23 mmol) of potassium carbonate and 3.7 g (46 mmol) of copper(II) oxide are added under nitrogen to a solution of 4.97 g (1.45 mmol) of the compound from Example 11 in 25 ml of dimethylformamide. The reaction mixture is heated overnight in a preheated oil bath (120° C.). The solvent is then removed by distillation in vacuo, and the residue is dissolved in water and the solution is washed with ether. The aqueous phase is acidified with dilute hydrochloric acid, washed with ethyl acetate, and the ethyl acetate phase is dried over sodium sulphate and concentrated in vacuo. The residue is dissolved in 20 ml of methanol and stirred overnight with 1 ml of conc. hydrochloric acid. The mixture is concentrated in vacuo, the residue is dissolved in aqueous sodium hydrogen carbonate solution and washed with ether, and the aqueous phase is acidified with dilute hydrochloric acid and washed with ether. This ether phase is washed with aqueous sodium chloride solution, dried over sodium sulphate and concentrated in vacuo.

Yield: 1.97 g (40.9% of theory) of foam $^1$H-NMR (CDCl$_3$): δ=2.45 (s, 3H); 2.6 (br, 1H); 4.05 (s, 3H); 4.7 (s, 2H); 6.65 (d, 1H); 7.1-7.7 (m, 4H); 12.0 (s, 1H) ppm.

EXAMPLE 13

2-Dimethylthiocarbamoyloxy-3-methoxy-5-methylbenzaldehyde

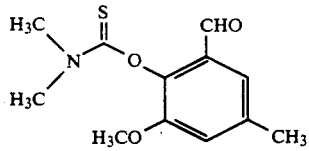

100 ml (0.8 mol) of dimethylthiocarbamoyl chloride in 150 ml of tetrahydrofuran are added at 5°-10° C. to 100 g (0.6 mol) of 2-hydroxy-3-methoxy-5-methylbenzaldehyde and 33.6 g (0.6 mol) of potassium hydroxide in 400 ml of water. The mixture is stirred at 25° C. for 15 min and, after adding 200 ml of 10% strength aqueous potassium hydroxide solution, extracted with ethyl acetate, the organic phase is washed with water and dried with sodium sulphate and, after concentrating in vacuo, the residue is recrystallised from ethanol.

Yield: 106.2 g (70% of theory)

$^1$H-NMR (CDCl$_3$): δ=2.4 (s, 3H); 3.4 (s, 3H); 3.5 (s, 3H); 3.85 (s, 3H); 7.0 (m, 1H); 7.3 (m, 1H); 10.05 (s, 1H) ppm.

EXAMPLE 14

2-Dimethylcarbamoylthio-3-methoxy-5-methylbenzaldehyde

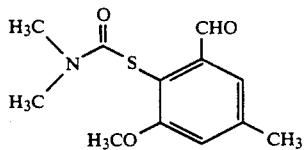

35.0 g (0.14 mol) of the compound from Example 13 are stirred at 240°-250° C. in 500 ml of diphenyl ether for 20 min. After cooling to 25° C., the diphenyl ether is eluted on silica gel using petroleum ether, then the product is eluted using ethyl acetate.

Yield: 19.7 g (55.6% of theory)

Melting point: 96°-98° C.

$^1$H-NMR (CDCl$_3$): δ=2.4 (s, 3H); 3.0 (s, 3H); 3.2 (s, 3H); 3.9 (s, 3H); 7.0 (s, 1H); 7.45 (s, 1H); 10.45 (s, 1H) ppm.

EXAMPLE 15

2-Hydroxymethyl-6-methoxy-4-methylthiophenol

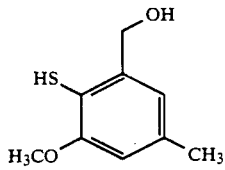

59 g (0.23 mol) of the compound from Example 14 are reduced with 11.4 g (0.3 mol) of lithium aluminium hydride analogously to Example 6.

Yield: 43 g of crude product (100% of theory)

EXAMPLE 16

2-Tributylstannyloxymethyl-6-methoxy-4-methyl-S-tributylstannylthiophenol

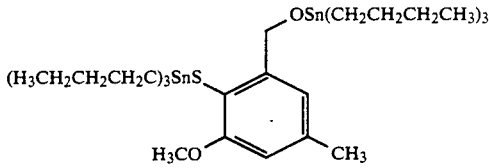

10 g (54.3 mmol) of the compound from Example 15 are stirred at 0° to 25° C. with 4 g (163 mmol) of sodium hydride and 31 ml (114 mmol) of tributyltin chloride in 300 ml of tetrahydrofuran until evolution of hydrogen is complete and the mixture is then heated under reflux overnight. It is cautiously hydrolysed with water and washed with ether, and the combined organic phases are dried using sodium sulphate and concentrated in vacuo.

Yield: 39.6 g of oil (95.6% of theory)

$^1$H-NMR (CDCl$_3$): δ=0.8-1.7 (m, 54H); 2.35 (s, 3H); 3.2 (t, 1H); 3.85 (s, 3H); 4.75 (d, 2H); 6.6 (s, 1H); 6.8 (s, 1H) ppm.

EXAMPLE 17

Methyl 5-formyl-6-methoxy-2-[2-hydroxymethyl-6-methoxy-4-methylphenylthio]benzoate

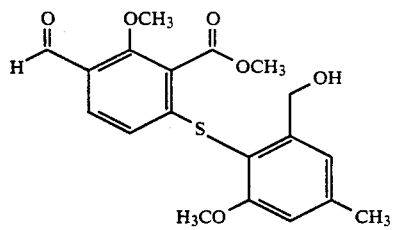

1.08 g (3.94 mmol) of the compound from Example 5 and 2 g (2.6 mmol) of the compound from Example 16 and 30 mg of tetrakis(triphenylphosphine)palladium are heated under reflux in 40 ml of toluene under a nitrogen atmosphere for 50 h. After concentrating in vacuo, the residue is taken up in acetonitrile and washed five times with pentane. The acetonitrile phase is concentrated in vacuo and the remaining oil (1.33 g) is chromatographed on a silica gel column using ethyl acetate/petroleum ether 1:5.

Yield: 360 mg of solid (36.2% of theory)

$^1$H-NMR (CDCl$_3$): $\delta$=2.45 (s, 3H); 3.8 (s, 3H); 4.0 (2s, 6H); 4.75 (d, 2H); 6.55 (d, 1H); 6.75 (s, 1H); 7.05 (s, 1H); 7.6 (d, 1H); 10.2 (s, 1H) ppm.

212 mg (26.1% of theory) of methyl 5-formyl-6-methoxy-2-[2-formyl-6-methoxy-4-methylphenylthio]benzoate

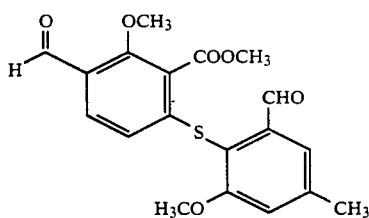

are obtained as a by-product.

$^1$H-NMR (CDCl$_3$): $\delta$=2.5 (s, 3H); 3.8 (s, 3H); 4.0 (2s, 6H); 6.55 (d, 1H); 7.05 (s, 1H); 7.5 (s, 1H); 7.65 (d, 1H); 10.25 (s, 1H); 10.6 (s, 1H) ppm.

EXAMPLE 18

5-Formyl-6-methoxy-2-[2-hydroxymethyl-6-methoxy-4-methylphenylthio]benzoic acid

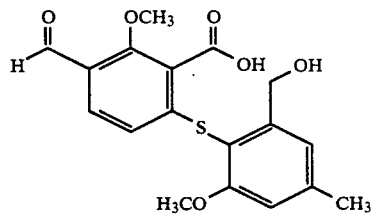

302 mg (0.8 mol) of the compound from Example 17 are dissolved in 4.6 ml of methanol and stirred at 25° C. with 36 mg of p-toluenesulphonic acid for 1 h. After addition of 0.45 g of potassium hydroxide, the mixture is heated under reflux overnight. It is concentrated in vacuo, and the residue is adjusted to pH=3 using dilute hydrochloric and washed with ethyl acetate. The organic phase is dried using sodium sulphate and concentrated in vacuo.

Yield: 273 mg of solid (94% of theory)

$^1$H-NMR (DMSO): $\delta$=2.4 (s, 3H); 3.7 (s, 3H); 3.95 (s, 3H); 4.5 (s, 2H); 6.35 (d, 1H); 6.95 (s, 1H); 7.1 (s, 1H); 7.55 (d, 1H); 10.1 (s, 1H) ppm.

Preparation Examples

EXAMPLE I

3-Formyl-4-methoxy-9-methyl-7H-dibenz[c,f][1,5]oxathiocin-5-one

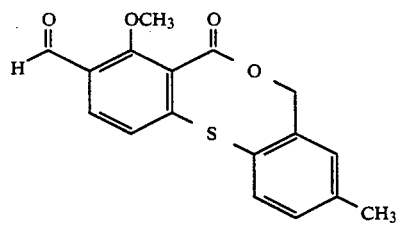

A solution of 1.97 mg (5.92 mmol) of the compound from Example 12 and 6.5 ml (47.3 mmol) of triethylamine in 380 ml of absolute acetonitrile is added dropwise to a solution of 5.3 g (23.7 mmol) of 2-chloro-1-methylpyridinium iodide in 380 ml of absolute acetonitrile over a period of 6 h. After a further hour at 80° C., the mixture is concentrated in vacuo, the residue is taken up in dichloromethane, and the solution is washed with water, dried over magnesium sulphate and concentrated. Purification is carried out by column chromatography on silica gel using petroleum ether/ethyl acetate 2:1.

Yield: 700 mg (37.6% of theory) of solid $^1$H-NMR (CDCl$_3$): $\delta$=2.3 (s, 3H); 4.1 (s, 3H); 5.25 (s, 2H); 6.95 (s, 1H); 7.1 (d, 1H); 7.4 (d, 1H); 7.55 (d, 1H); 7.9 (d, 1H) ppm.

EXAMPLE II 3-(1-Hydroxy-3-methylbutyl)-4-methoxy-9-methyl-7H-dibenz[c,f][1,5]oxathiocin-5-one

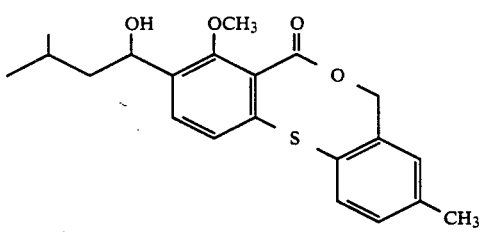

660 mg (2.1 mmol) of the compound from Example I in 10 ml of absolute tetrahydrofuran are treated under argon at 0° C. with 1.2 ml (2.3 mmol) of a 2M isobutyryl-magnesium bromide solution in tetrahydrofuran and the mixture is stirred at 25° C. for 1 h. After addition of 2 ml of 1N hydrochloric acid, the mixture is diluted with methylene chloride, washed with water, dried and evaporated. After chromatographic purification on silica gel Si60 (petroleum ether/ethyl acetate 5:1), 121 mg (15% of theory) of the main product are obtained as a colourless solid.

$^1$H-NMR (CDCl$_3$): $\delta$=1.0 (t, 6H); 1.45 (m, 1H); 1.6–1.9 (m, 2H); 1.95 (d, 1H); 2.3 (s, 3H); 3.95 (s, 1H); 5.1 (m, 1H); 5.15 (s, 2H); 6.85 (s, 1H); 7.1 (d, 1H); 7.35 (d, 1H); 7.45 (d, 1H) 7.6 (d, 1H).

EXAMPLE III 322 mg of 3-hydroxymethyl-4-methoxy-9-methyl-7H-dibenz[c,f][1,5]oxathiocin-5-one

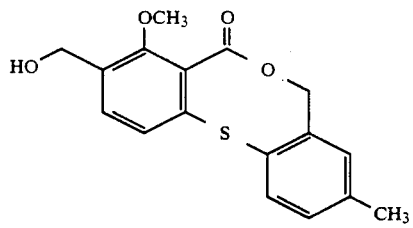

are isolated as a by-product.

$^1$H-NMR (CDCl$_3$): δ=2.0 (t, 1H); 2,3 (s, 3H); 3.95 (s, 3H); 4.8 (d, 2H); 5.15 (s, 2H); 6.85 (s, 1H); 7.1 (d, 1H); 7.35–7.6 (m, 3H) ppm.

EXAMPLE IV

3-Formyl-4,11-dimethoxy-9-methyl-7H-dibenz[c,f][1,5]oxathiocin-5-one

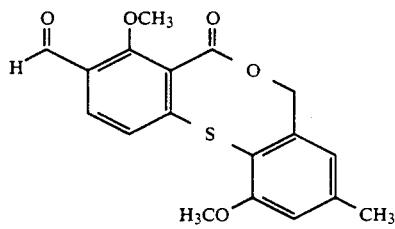

9.9 mg of product are obtained analogously to Example I from 128 mg (0.35 mmol) of the compound from Example 18.

Yield: 8% of theory $^1$H-NMR (CDCl$_3$): δ=2.3 (s, 3H); 3.9 (s, 3H); 4.1 (s, 3H); 5.2 (s, 2H); 6.55 (s, 1H); 6.75 (s, 1H); 7.55 (d, 1H); 7.95 (d, 1H); 10.4 (s, 1H); ppm.

EXAMPLE V 3-(1-Hydroxy-3-methylbutyl)-4,11-dimethoxy-9-methyl-7H-dibenz[c,f][1.5]oxathiocin-5-one

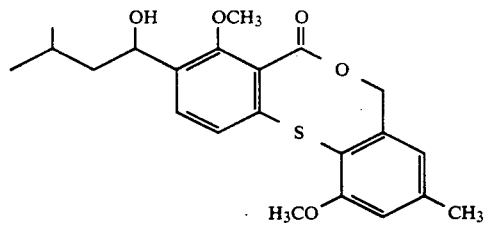

4 mg of colourless solid are obtained analogously to Example II from 9.9 mg (0.03 mmol) of the compound from Example IV.

Yield: 34% of theory $^1$H-NMR (CDCl$_3$): δ=0.9 (m, 6H); 1.5 (m, 3H); 2.3 (s, 3H); 3.9 (s, 3H); 4.0 (s, 3H); 4.95 (m, 1H); 5.1 (m, 2H); 6.5 (s, 1H); 6.8 (s, 1H); 7.45 (d, 1H); 7.6 (d, 1H) ppm.

EXAMPLE VI 3.5 mg (30% of theory) of 3-hydroxymethyl-4,11-dimethoxy-9-methyl-7H-dibenz[c,f][1,5]oxathiocin-5-one

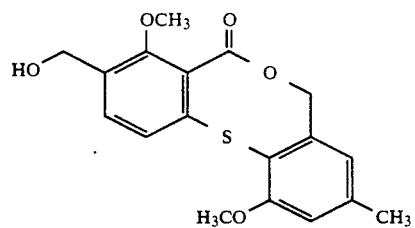

are isolated as a by-product.

$^1$H-NMR (CDCl$_3$): δ=2.35 (s, 3H), 3.9 (s, 3H); 4.0 (s, 3H); 4.75 (s, 2H); 5.1 (s, 2H); 6.5 (s, 1H); 6.85 (s, 1H); 7.5 (q, 2H) ppm.

EXAMPLE VII 3-(1-Hydroxy-2-methylpropyl)-4-methoxy-9-methyl-7H-dibenz[c,f][1,5]oxathiocin-5-one

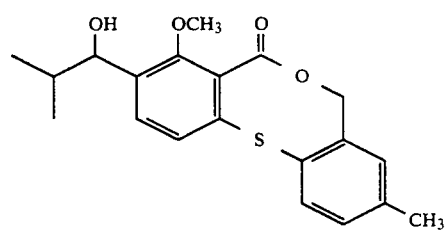

63.8 mg of the title compound are obtained analogously to Example II from 250 mg (0.8 mmol) of the compound from Example I and 0.44 ml (0.88 mmol) of a 2 molar solution of isopropylmagnesium chloride in ether.

Yield: 22.4% of theory $^1$H-NMR (CDCl$_3$): δ=0.8 (d, 3H); 1.0 (d, 3H); 2.0 (m, 1H); 2.3 (s, 3H); 3.95 (s, 3H); 4.7 (m, 1H); 5.15 (s, 2H); 6.9 (s, 1H); 7.1 (d, 2H); 7.4 (m, 2H); 7.55 (d, 2H) ppm.

EXAMPLE VIII

3-Carboxy-4,11-dimethoxy-9-methyl-7H-dibenz[c,f][1,5]oxathiocin-5-one

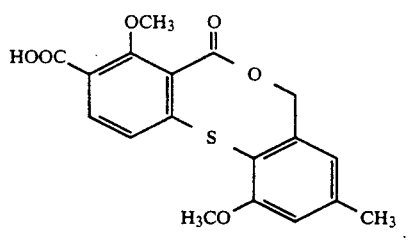

560 mg (1.62 mmol) of the compound from Example VI are stirred overnight at 25° C. with 9.13 g (24.3 mmol) of pyridinium dichromate in 20 ml of dimethylformamide. The mixture is poured into water and washed with ether, the ether phase is washed with water and dried over sodium sulphate and, after concentrating in vacuo, the residue is chromatographed on silica gel using methylene chloride/ethanol 10:1.

Yield: 310 mg of solid (53% of theory)

$^1$H-NMR (DMSO): δ=2.25 (s, 3H); 3.85 (2d, 6H); 5.1 (s, 2H); 6.65 (s, 1H); 6.95 (s, 1H); 7.3 (d, 2H); 7.55 (d, 1H) ppm.

EXAMPLE IX

3-Formyl-4,11-dimethoxy-9-methyl-7H-dibenz[c,f][1,5]oxathiocin-5-one-12,12-dioxide

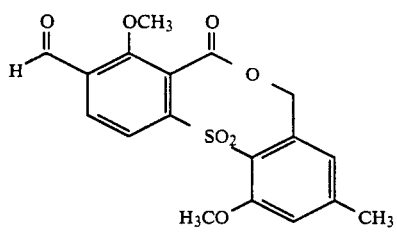

50 mg (0.15 mmol) of the compound from Example IV are stirred at 25° C. with 65 mg (0.32 mmol) of metachloroperbenzoic acid (80% strength) in 10 ml of methylene chloride. The mixture is diluted with methylene chloride and the organic phase is washed several times with sodium thiosulphate solution, sodium carbonate solution and water. After drying with sodium sulphate and concentrating the methylene chloride solution, 56 mg of colourless foam are obtained.

Yield: 97.6% of theory
$^1$H-NMR (CDCl$_3$): δ=2.4 (s, 3H); 3.95 (s, 3H); 4.15 (s, 3H); 5.45 (m, 2H); 6.8 (s, 1H); 6.9 (s, 1H); 8.1 (d, 1H); 8.2 (d, 1H) ppm.

EXAMPLE X 3-(1-Hydroxy-3-methylbutyl)-4,11-dimethoxy-9-methyl-7H-dibenz[c,f][1,5]oxathiocin-5-one-12,12-dioxide

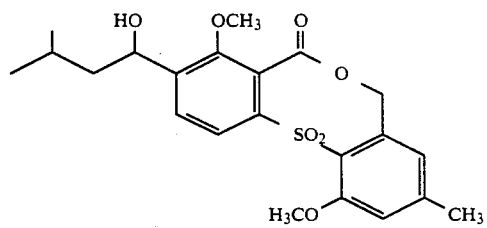

8 mg of the title compound are obtained analogously to Example II from 50 mg of the compound from Example IX.

Yield: 13.8% of theory
$^1$H-NMR (CDCl$_3$): δ=1.0 (m, 6H); 1.4–2.0 (m, 3H); 2.4 (s, 3H); 3.95 (s, 3H); 4.0 (s, 3H); 5.1 (m, 1H); 5.3 (m, 2H); 6.7 (s, 1H); 6.9 (s, 1H); 7.8 (d, 1H); 8.05 (d, 1H) ppm.

In addition 18.1 mg of

EXAMPLE XI

3-Hydroxymethyl-4,11-dimethoxy-9-methyl-7H-dibenz[c,f][1,5]oxathiocin-5-one-12,12-dioxide

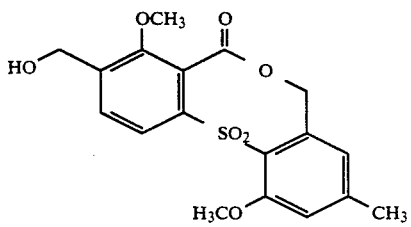

are isolated.

Yield: 35.9% of theory
$^1$H-NMR (CDCl$_3$): δ=2.35 (s, 3H); 3,95 (s, 3H); 4.0 (s, 3H); 4.85 (m, 2H); 5.3 (m, 2H); 6.7 (s, 1H); 6.85 (s, 1H); 7.8 (d, 1H); 8.1 (d, 1H) ppm.

EXAMPLE XII 3-(1-Hydroxy-2-methylpropyl)-4-methoxy-9-methyl-7H-dibenz[c,f][1,5]oxathiocin-5-one-12,12-dioxide.

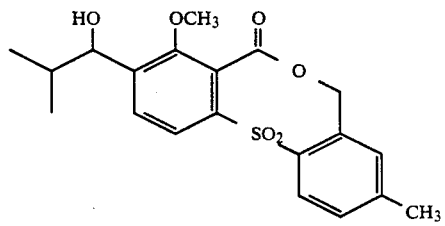

52 mg of the title compound are obtained analogously to Example IX from 61.4 mg (0.17 mmol) of the compound from Example VII.

Yield: 77% of theory
$^1$H-NMR (CDCl$_3$): δ=0.9 (2d, 6H); 2.0 (m, 1H); 2.4 (s, 3H); 4.0 (s, 3H); 4.8 (m, 1H); 5.4 (m, 2H); 7.2 (s, 1H); 7.35 (d, 1H); 7.75 (d, 1H); 8.05 (d, 1H); 8.15 (d, 1H) ppm.
MS (CI): 408 (M+NH$_4$+): 390, 373; 364; 347

The compound from Example II is resolved into the two enantiomers (Example XIII and Example XIV) under HPLC conditions (24 bar) on a CHIRACEL ® OJ column using hexanol/2-propanol mixtures;

EXAMPLE XIII (+)-3-(1-Hydroxy-3-methylbutyl)-4-methoxy-9-methyl-7H-dibenz[c,f][1,5]oxathiocin-5-one

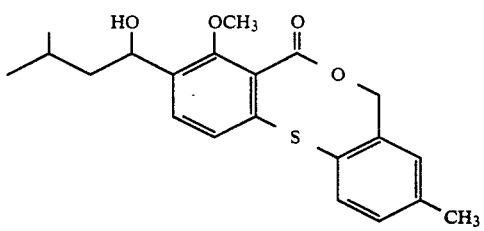

[α]$_D^{20}$= +22.2° (c=1 in 2-propanol)

EXAMPLE XIV (−)-3-(1-Hydroxy-3-methylbutyl)-4-methoxy-9-methyl-7H-dibenz[c,f][1,5]oxathiocin-5-one

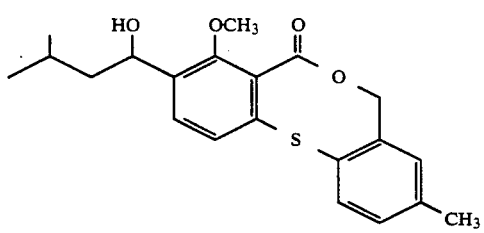

[α]$_D^{20}$= −20.1° (c=1 in 2-propanol)

EXAMPLE XV

8-Bromo-3-(1-hydroxy-3-methylbutyl)-4,11-dimethoxy-9-methyl-7H-dibenz[c,f][1,5]oxathiocin-5-one

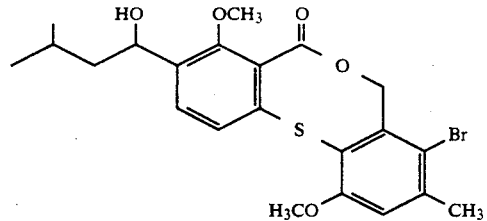

12.8 μl (0.25 mmol) of bromine are added to a solution of 50 mg (0.13 mmol) of the compound from Example V and 33.6 mg (0.13 mmol) of iron(III) chloride trihydrate in 1 ml of ethanol/water (3:1) and the mixture is stirred at 25° C. overnight. After diluting with methylene chloride and washing with 10% strength potassium iodide solution and water, the solution is dried with sodium sulphate and concentrated, and the residue is chromatographed on silica gel using ethyl acetate/petroleum ether (1:5).

Yield: 37 mg of foam (62% of theory)

$^1$H-NMR (CDCl$_3$): δ=1.0 (m, 6H); 1.4-1.9 (m, 3H); 2.0 (d, 1H); 2.4 (s, 3H); 3.9 (s, 3H); 4.0 (s, 3H); 5.1 (m, 1H); 5.6 (s, 2H); 6.8 (s, 1H); 7.45 (d, 1H); 7.6 (d, 1H) ppm.

EXAMPLE XVI 3-(1-Hydroxy-3-methylbutyl)-4,11-dimethoxy-9-methyl-7H-dibenz[c,f][1,5]oxathiocin-5-one-12-oxide

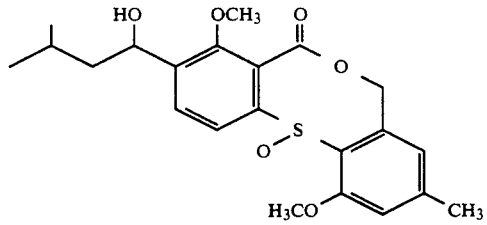

32 mg (0.08 mmol) of the compound from Example V are reacted with 16 mg (0.08 mmol) of metachloroperbenzoic acid (80 to 90% strength) analogously to Example IX.

In addition to 7.7 mg of starting material (Example I) and 10 mg of the sulphone (Example X), 22 mg of the title compound are obtained.

Yield: 65.7% of theory $^1$H-NMR (CDCl$_3$): δ=0.95 (m, 6H); 1.4-1.9 (m, 3H); 2.3 (s, 3H); 3.75 (s, 3H); 3.95 (s, 3H); 5.1 (m, 1H); 5.45 (q, 2H); 6.65 (s, 1H); 6.7 (s, 1H); 7.7-8.0 (m, 2H) ppm. MS (EI): 418; 402; 357

The compound from Example XV was resolved into the two enantiomers (Examples XVII and XVIII) analogously to Examples XIII and XIV:

EXAMPLE XVII (+)-8-Bromo-3-(1-hydroxy-3-methylbutyl)-4,11-dimethoxy-9-methyl-7H-dibenz[c,f][1,5]oxathiocin-5-one

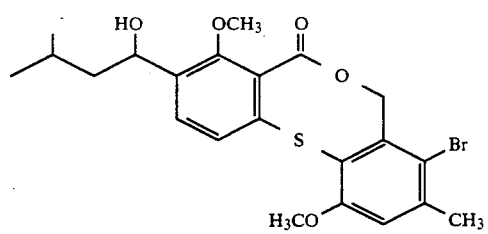

[α]$_D^{20}$= +8.76° (c=1 in methanol)

EXAMPLE XVIII (−)-8-Bromo-3-(1-hydroxy-3-methylbutyl)-4,11-dimethoxy-9-methyl-7H-dibenz[c,f][1,5]oxathiocin-5-one

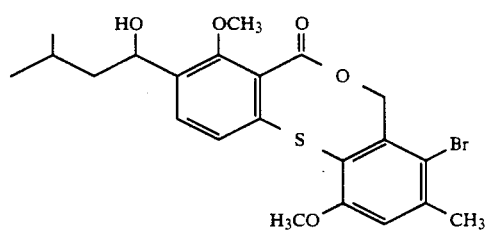

[α]$_D^{20}$= −4.87° (c=1 in methanol)

EXAMPLE XIX (+)-8-Bromo-3-(1-hydroxy-3-methylbutyl)-4,11-dimethoxy-9-methyl-7H-dibenz[c,f][1,5]oxathiocin-5-one-12,12-dioxide

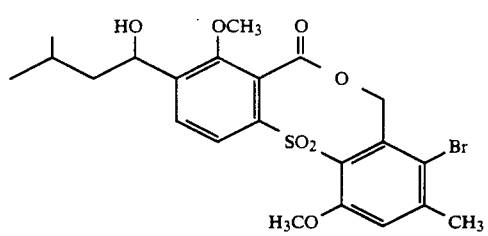

403.8 mg (0.84 mmol) of the compound from Example XVII are reacted with 170.5 mg (0.84 mmol) of metachloroperbenzoic acid (80–90% strength) analogously to Example IX and the mixture is chromatographed on 75 g of silica gel using dichloromethane/ethyl acetate (20:1).

In addition to 43.7 mg of starting material (10% of theory), 35 mg (8% of theory) of the title compound and 280 mg (67% of theory) of the compound from Example XX are obtained.

MS (EI): 514, 512 (M+) 457, 455

[α]$_D^{20}$= +12.63° (c=1 in methanol)

EXAMPLE XX (+)-8-Bromo-3-(1-hydroxy-3-methylbutyl)-4,11-dimethoxy-9-methyl-7H-dibenz[c,f][1,5]oxathiocin-5-one-12-oxide (diastereomer mixture)

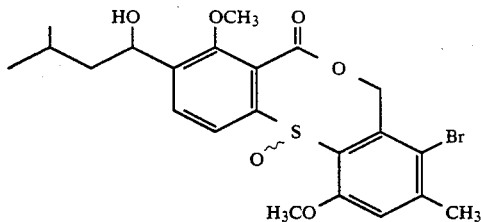

This title compound was obtained as described under Example XIX.

EXAMPLE XXI (−)-8-Bromo-3-(1-hydroxy-3-methylbutyl)-4,11-dimethoxy-9-methyl-7H-dibenz[c,f][1,5]oxathiocin-5-one-12,12-dioxide

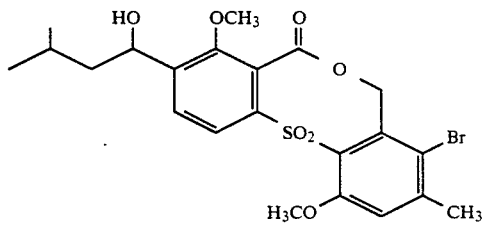

113 mg (23.8% of theory) of the title compound are obtained in addition to 7% starting material from 445 mg (0.952 mmol) of the compound from Example XVIII analogously to Example XIX.

$[\alpha]_D^{20} = -18.03°$ (c=1 in methanol)

In addition, 330 mg (69.5% of theory) of the compound from

EXAMPLE XXII (−)-8-Bromo-3-(1-hydroxy-3-methylbutyl)-4,11-dimethoxy-9-methyl-7H-dibenz[c,f][1,5]oxathioxin-5-one-12-oxide (diastereomer mixture)

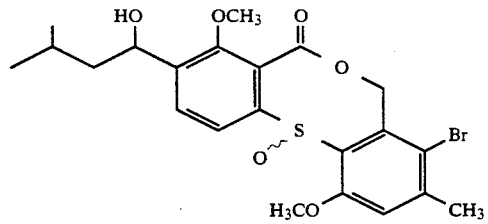

were obtained.

EXAMPLES XXIII–XXXI

Analogously to Example XIX, 291.8 mg (20.1% of theory) of the racemic sulphoxide from Example XXIII:

EXAMPLE XXIII (+)-3-(1-Hydroxy-3-methylbutyl)-4-methoxy-9-methyl-7H-dibenz[c,f][1,5]oxathiocin-5-one-12-oxide (1st diastereomer)

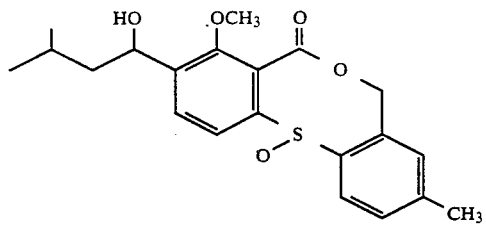

are obtained from 1.39 g (3.74 mmol) of the compound from Example II after chromatography on 150 g of silica gel using ethyl acetate/petroleum ether 1:4 in addition to 242.1 mg (17.3% of theory) of the starting material and a mixed fraction (657 mg).

MS(EI): 388 (M+) 331, 151

Melting point: 146°–160° C.

By chromatography of the mixed fraction on 150 g of silica gel using dichloromethane/ethyl acetate 20:1, 290 mg (20% of theory) of the racemic sulphone from Example XXIV and 304 mg (20.9% of theory) of the racemic sulphoxide from Example XXV (2nd diastereomer) are obtained:

EXAMPLE XXIV (±)-3-(1-Hydroxy-3-methylbutyl)-4-methoxy-9-methyl-7H-dibenz[c,f][1,5]oxathiocin-5-one-12,12-dioxide

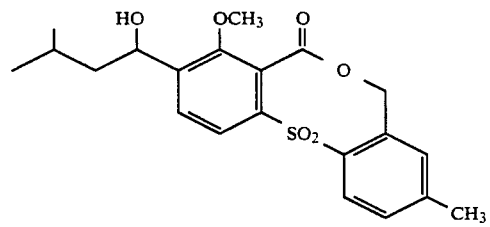

MS(EI) 422 (M+NH$_4^+$), 404 (M+), 378, 364, 347

EXAMPLE XXV (±)-3-(1-Hydroxy-3-methylbutyl)-4-methoxy-9-methyl-7H-dibenz[c,f][1,5]oxathiocin-5-one-12-oxide (2nd diastereomer)

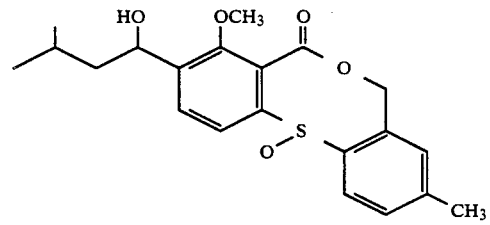

MS(DCI) 389 (M+H+), 331

Melting point: 166°–170° C.

The racemic compounds from Examples XXIII to XXV were resolved into the enantiomers analogously to Examples XIII/XIV:

EXAMPLE XXVI (+)-3-(1-Hydroxy-3-methylbutyl)-4-methoxy-9-methyl-7H-dibenz[c,f][1,5]oxathiocin-5-one-12-oxide (1st diastereomer)

$[\alpha]_D^{20} = +260.54°$ (c=1 in methanol)

EXAMPLE XXVII (−)-3-(1-Hydroxy-3-methylbutyl)-4-methoxy-9-methyl-7H-dibenz[c,f][1,5]oxathiocin-5-one-12-oxide (1st diastereomer)

[α]$_D^{20}$ = −256.66° (c=1 in methanol)

EXAMPLE XXVIII (+)-3-(1-Hydroxy-3-methylbutyl)-4-methoxy-9-methyl-7H-dibenz[c,f][1,5]oxathiocin-5-one-12-oxide (2nd diastereomer)

[α]$_D^{20}$ = +197.09° (c=1 in methanol)

EXAMPLE XXIX (−)-3-(1-Hydroxy-3-methylbutyl)-4-methoxy-9-methyl-7H-dibenz[c,f][1,5]oxathiocin-5-one-12-oxide (2nd diastereomer)

[α]$_D^{20}$ = −202.02° (c=1 in methanol)

EXAMPLE XXX (+)-3-(1-Hydroxy-3-methylbutyl)-4-methoxy-9-methyl-7H-dibenz[c,f][1,5]oxathiocin-5-one-12,12-dioxide

[α]$_D^{20}$ = +1.47° (c=1 in methanol)

EXAMPLE XXXI (−)-3-(1-Hydroxy-3-methylbutyl)-4-methoxy-9-methyl-7H-dibenz[c,f][1,5]oxathiocin-5-one-12,12-dioxide

[α]$_D^{20}$ = −1.52° (c=1 in methanol)

EXAMPLE XXXII

8-Bromo-4,11-dimethoxy-9-methyl-3-(3-methylbutan-1-oyl)-7H-dibenz[c,f][1,5]oxathiocin-5-one

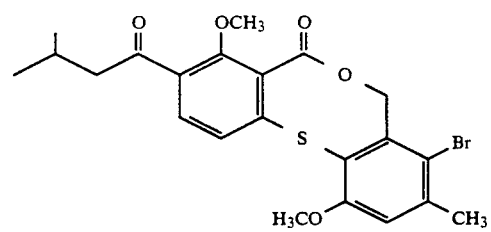

31 mg (0.15 mmol) of pyridinium chlorochromate are added to a solution of 35 mg (0.07 mmol) of the compound from Example XV in 4 ml of dichlormethane and the mixture is stirred at room temperature for 2 hours. The reaction solution is applied to silica gel, eluted with dichloromethane and chromatographed on silica gel using petroleum ether/ethyl acetate 1:3.

Yield: 31.1 mg (93% of theory)

MS(EI): 480, 478 (M+), 452, 450, 425, 422

EXAMPLE XXXIII (±)-3-(1-Hydroxy-3-methyl-3-buten-1-yl)-4,11-dimethoxy-9-methyl-7H-dibenz[c,f][1,5]oxathiocin-5-one

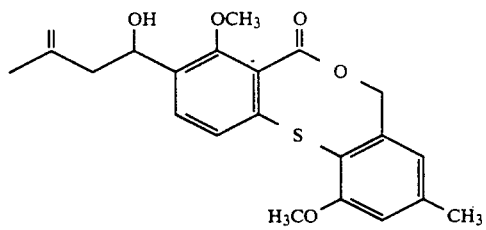

83 mg of the title compound are obtained from 70 mg (0.2 mmol) of the compound from Example IV and methallylmagnesium chloride analogously to Example II.

Yield: 100% of theory

MS(EI): 400 (M+), 345, 327, 315, 299

EXAMPLE XXXIV (±)-3-(1-Hydroxy-3-methyl-3-buten-1-yl)-4-methoxy-9-methyl-7H-dibenz[c,f][1,5]oxathiocin-5-one

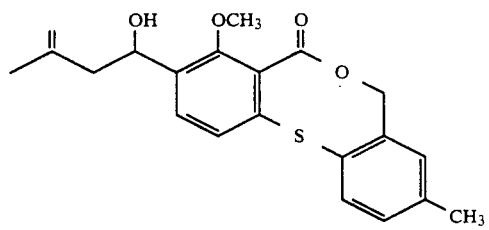

594.9 mg of the title compound are obtained from 1.43 g (4.55 mmol) of the compound from Example I and methallylmagnesium chloride analogously to Example II.

Yield: 35.3% of theory $^1$H-NMR (CDCl$_3$): δ=1.8 (s, 3H); 2.3 (s, 3H); 2.2–2.5 (m, 2H); 3.95 (s, 3H); 4.85 (m, 1H); 4.95 (m, 1H); 5.15 (m, 3H); 6.85 (s, 1H); 7.1 (d, 1H); 7.35 (d, 1H); 7.45 (d, 1H); 7.65 (d, 1H); ppm.

We claim:

1. A dibenz-oxa-thiazinone of the formula I

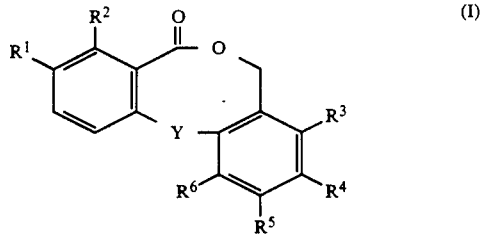

in which

R$^1$ and R$^6$ are identical or different and each represent hydrogen; or represent straight-chain or branched alkyl or alkenyl each having up to 10 carbon atoms which are optionally monosubstituted to trisubstituted by halogen, azido or imino or by cycloalkyl having 3 to 8 carbon atoms or aryl having 6 to 10 carbon atoms, which in turn are optionally monosubstituted or disubstituted by identical or different substituents selected from the group consisting of halogen, nitro, cyano, hydroxyl and straight-chain or branched alkyl, alkoxy or alkoxycarbonyl each having up to 6 carbon atoms; or represent alkyl or alkenyl which are optionally additionally substituted by a group of the formula —$OR^7$, —CO—$R^8$ or —$CONR^9R^{10}$, in which $R^7$ denotes hydrogen, cycloalkyl having 3 to 7 carbon atoms or straight-chain or branched alkyl, alkenyl or acyl each having up to 8 carbon atoms, which are optionally monosubstituted to trisubstituted by halogen-substituted phenyl, cycloalkyl having 3 to 7 carbon atoms, hydroxyl, halogen or straight-chain or branched alkoxy having up to 6 carbon atoms or by carboxyl, acyl having up to 6 carbon atoms or alkoxycarbonyl having up to 6 carbon atoms, $R^8$ denotes hydrogen, hydroxyl, phenoxy or straight-chain or branched alkoxy having up to 8 carbon atoms, or denotes aryl having 6 to 10 carbon atoms or cycloalkyl having 3 to 8 carbon atoms, which are optionally substituted by hydroxyl or halogen or by straight-chain or branched alkyl, alkoxy or alkoxycarbonyl each having up to 8 carbon atoms, or denotes straight-chain or branched alkyl or alkenyl each having up to 8 carbon atoms, which are optionally substituted by halogen, carboxyl, hydroxyl or alkoxy, alkoxycarbonyl or acyl each having up to 6 carbon atoms, $R^9$ and $R^{10}$ are identical or different and denote hydrogen, straight-chain or branched alkyl having up to 8 carbon atoms or denote phenyl, or $R^1$ and/or $R^6$ directly represent a group of the formula —$OR^7$ or —CO—$R^8$, in which $R^7$ and $R^8$ have the abovementioned meaning, $R^2$ represents hydrogen, or represents the group —$OR^7$, in which $R^7$ has the abovementioned meaning, or represents straight-chain or branched alkyl or alkenyl each having up to 8 carbon atoms, which are optionally substituted by the group —$OR^7$, in which $R^7$ has the abovementioned meaning, or represents phenyl which is optionally monosubstituted to trisubstituted by halogen, nitro or hydroxyl or by straight-chain or branched alkoxy having up to 6 carbon atoms, $R^3$, $R^4$ and $R^5$ are identical or different and represent hydrogen, nitro, halogen or straight-chain or branched alkyl having up to 8 carbon atoms, Y represents a sulphur atom or a group of the formula >SO or >$SO_2$, and their physiologically acceptable salts, with the proviso that if Y represents the >SO— or >$SO_2$-group, at least one of the substituents $R^1$-$R^6$ must be different from hydrogen.

2. A compound according to claim 1, in which $R^1$ and $R^6$ are identical or different and represent hydrogen or straight-chain or branched alkyl or alkenyl each having up to 8 carbon atoms which are optionally monosubstituted or disubstituted by fluorine, chlorine, bromine or iodine or by cyclopropyl, cyclopentyl, cyclohexyl or phenyl, which in turn are optionally substituted by fluorine, chlorine or hydroxyl or by straight-chain or branched alkyl or alkoxy each having up to 4 carbon atoms, or alkyl or alkenyl which are optionally additionally substituted by a group of the formula —$OR^7$, —CO—$R^8$ or —$CONR^9R^{10}$, in which $R^7$ denotes hydrogen, cyclopentyl, cyclohexyl or straight-chain or branched alkyl or acyl each having up to 6 carbon atoms, which are optionally substituted by chlorine-substituted phenyl, cyclopropyl, cyclopentyl, cyclohexyl, hydroxyl, fluorine, chlorine, bromine or straight-chain or branched alkoxy having up to 4 carbon atoms or by carboxyl, acyl or alkoxycarbonyl having up to 6 carbon atoms, $R^8$ denotes hydrogen, hydroxyl, phenoxy or straight-chain or branched alkoxy having up to 6 carbon atoms, or denotes phenyl, cyclopropyl, cyclopentyl or cyclohexyl, which are optionally substituted by hydroxyl, fluorine, chlorine or bromine or by straight-chain or branched alkyl or alkoxy each having up to 6 carbon atoms, or denotes straight-chain or branched alkyl having up to 6 carbon atoms, which is optionally substituted by fluorine, chlorine, bromine, hydroxyl or carboxyl or by alkoxy, acyl or alkoxycarbonyl having up to 6 carbon atoms, $R^9$ and $R^{10}$ are identical or different and denote hydrogen, straight-chain or branched alkyl having up to 6 carbon atoms, or $R^1$ and/or $R^6$ directly represent a group of the formula —$OR^7$ or —CO—$R^8$, in which $R^7$ and $R^8$ have the abovementioned meaning, $R^2$ represents hydrogen or the group —$OR^7$, in which $R^7$ has the abovementioned meaning, or represents straight-chain or branched alkyl having up to 6 carbon atoms, which is optionally substituted by the group —$OR^7$, in which $R^7$ has the abovementioned meaning, or represents phenyl which is optionally substituted by fluorine, chlorine, bromine, iodine, hydroxyl or straight-chain or branched alkoxy having up to 4 carbon atoms, $R^3$, $R^4$ and $R^5$ are identical or different and represent hydrogen, nitro, fluorine, chlorine, bromine, iodine or straight-chain or branched alkyl having up to 6 carbon atoms, Y represents a sulphur atom or a group of the formula >SO or >$SO_2$, and their physiologically acceptable salts, with the proviso that if Y represents the >SO— or >$SO_2$-group, at least one of the substituents $R^1$-$R^6$ must be different from hydrogen.

3. A compound according to claim 1, in which $R^1$ and $R^6$ are identical or different and represent hydrogen or straight-chain or branched alkyl or alkenyl having up to 8 carbon atoms, which is optionally monosubstituted or disubstituted by fluorine, chlorine, bromine, iodine or phenyl, which in turn can be substituted by chlorine, hydroxyl, methyl or methoxy, or alkenyl or alkyl which are optionally additionally substituted by a group of the formula —$OR^7$, —CO—$R^8$ or —$CONR^9R^{10}$, in which $R^7$ denotes hydrogen, cyclopentyl or straight-chain or branched alkyl or acyl having up to 4 carbon atoms which are optionally substituted by chlorine-substituted phenyl, hydroxyl, chlorine or methoxy or by carboxyl, acyl or alkoxy carbonyl each having up to 4 carbon atoms, $R^8$ denotes hydrogen, hydroxyl or straight-chain or branched alkoxy having up to 4 carbon atoms, or denotes phenyl, cyclopropyl, cyclopentyl or cyclohexyl, which are optionally substituted by hydroxyl, fluorine, chlorine or bromine or by straight-chain or branched alkyl or alkoxy each having up to 4 carbon atoms, or denotes straight-chain or branched alkyl having up to 4 carbon atoms, which is optionally substituted by fluorine, chlorine or bromine or by hydroxyl, carboxyl, alkoxy, acyl or alkoxycarbonyl each having up to 4 carbon atoms, $R^9$ and $R^{10}$ are identical or different and denote hydrogen or straight-chain or branched alkyl having up to 4 carbon atoms, $R^1$ and/or $R^6$ directly represent a group of the formula $-OR^7$ or $-CO-R^8$, in which $R^7$ and $R^8$ have the abovementioned meaning, $R^2$ represents hydrogen or the group $-OR^7$, in which $R^7$ has the abovementioned meaning, or represents straight-chain or branched alkyl having up to 4 carbon atoms, which is optionally substituted by the group of the formula $-OR^7$, in which $R^7$ has the abovementioned meaning, or represents phenyl which is optionally substituted by fluorine, chlorine, bromine, iodine, hydroxyl or methoxy, $R^3$, $R^4$ and $R^5$ are identical or different and represent hydrogen, nitro, fluorine, chlorine, bromine or iodine, or represent straight-chain or branched alkyl having up to 4 carbon atoms, Y represents a sulphur atom or a group of the formula $>SO$ or $>SO_2$ and their physiologically acceptable salts, with the proviso that if Y represents the $>SO-$ or $>SO_2$-group, at least one of the substituents $R^1$-$R^6$ must be different from hydrogen.

4. A composition for treatment of a condition of the circulatory system comprising an amount effective therefor of a compound according to claims 1 and a pharmacologically acceptable diluent.

5. A method of treating a condition of the circulatory system in a patient in need thereof which comprises administering to such patient an amount effective therefor of a compound according to claim 1.

* * * * *